United States Patent [19]

Fukushima

[11] Patent Number: 4,635,645
[45] Date of Patent: Jan. 13, 1987

[54] ELECTRONIC SPHYGMOMANOMETER

[75] Inventor: Toshitaka Fukushima, Tokyo, Japan

[73] Assignee: Seiko Instruments & Electronics Ltd., Tokyo, Japan

[21] Appl. No.: 585,885

[22] Filed: Mar. 2, 1984

[30] Foreign Application Priority Data

| Mar. 3, 1983 [JP] | Japan | 58-34887 |
| Mar. 3, 1983 [JP] | Japan | 58-34888 |
| Mar. 3, 1983 [JP] | Japan | 58-34889 |
| Mar. 3, 1983 [JP] | Japan | 58-30883[U] |
| Mar. 3, 1983 [JP] | Japan | 58-30884[U] |

[51] Int. Cl.$^4$ ............................................. A61B 5/04
[52] U.S. Cl. .................................... 128/680; 128/700
[58] Field of Search ........ 128/670, 672, 677, 678–679, 128/680–683, 700

[56] References Cited

U.S. PATENT DOCUMENTS

| 3,101,082 | 8/1963 | Steen et al. | 128/680 |
| 3,773,033 | 11/1973 | Rodbard et al. | 128/700 X |
| 4,211,238 | 7/1980 | Shu et al. | 128/700 |
| 4,216,779 | 8/1980 | Squires et al. | 128/700 X |

FOREIGN PATENT DOCUMENTS 2054861 2/1981 United Kingdom ................ 128/670

Primary Examiner—Kyle L. Howell
Assistant Examiner—Angela D. Sykes
Attorney, Agent, or Firm—Robert E. Burns; Emmanuel J. Lobato; Bruce L. Adams

[57] ABSTRACT

In an electronic sphygmomanometer for a vehicle having a Korotkoff sound detecting circuit, a cuff pressure detecting circuit, a Korotkoff reference signal generator, a central processing unit for receiving the output of the Korotkoff sound detecting circuit, the output of the cuff pressure detecting circuit and the output of the Korotkoff reference signal generating and determining a systolic and diastolic blood pressure and a display unit for indicating the systolic and diastolic blood pressure, the electronic sphygmomanometer includes a cardioelectric potential detecting circuit having one-shot pulse generating circuit and the Korotkoff reference signal generator includes a flip-flop for receiving a cardioelectric potential synchronizing signal and pulse pressure variations signal so that the electronic sphygmomanometer mounted on the vehicle is not very much adversely affected by the vibration and noise.

14 Claims, 22 Drawing Figures

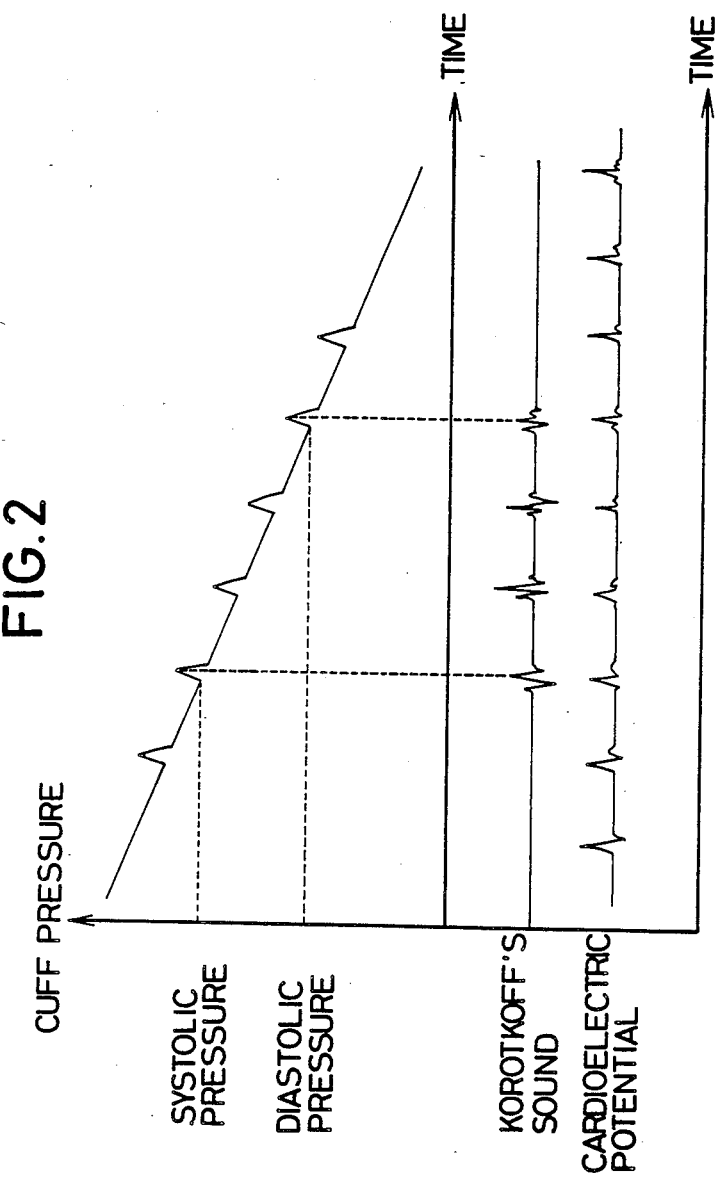

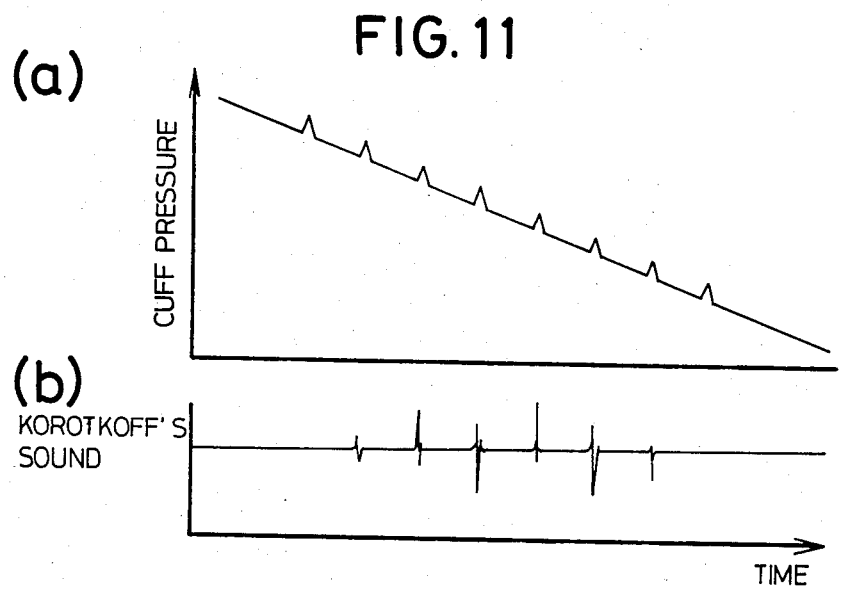
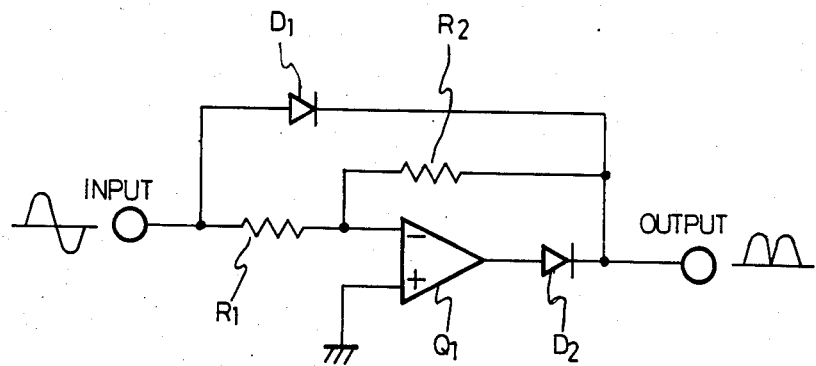

ELECTRONIC SPHYGMOMANOMETER

BACKGROUND OF THE INVENTION

This invention reates to an electronic sphygmomanometer, and more particularly to a heartbeat referring type electronic sphygmomanometer.

It is evident that the measurement of blood pressure is necessary for regular medical treatment and health control. The measurement of blood pressure is required even in more so emergency medical treatments. When a conventional sphygmomanometer is used in a moving ambulance during emergency medical treatment, it is very much adversely affected by vibration and noise, and often operates erroneously. Therefore, the blood pressure cannot be measured accurately in many cases. A generally-used blood pressure measuring system includes a Korotkoff sound detecting device.

In the normal measurement sequence, a cuff placed over the brachial artery is first inflated to well beyond the systolic blood pressure thereby cutting off all blood flow. The cuff is then allowed to deflate slowly. When the cuff pressure reaches the systolic pressure, the pulsatile blood flow just begins and Korotkoff sounds will be detected. When the cuff pressure is further reduced to the diastolic blood pressure, the flow is continuous and no Korotkoff sounds are detected.

It is assumed that the pressures at which the first and last Korotkoff sounds are detected will correspond to the systolic and diastolic blood pressures respectively. An electronic sphygmomanometer is designed to electronically carry out the above-described operation, and is adapted to detect pressure variations (which will be hereinafter referred to as "pulse pressure variations") based on a pulsatile blood pressure variation within a brachial artery to use as a Korotkoff sound reference signal (which will be hereinafter referred to as "reference signal") for determining the existence of Korotkoff sounds. When such a sphygmomanometer is used in a moving vehicle, a cuff and rubber tubes are subjected to unavoidable vibration, and the vibration sounds enter not only a Korotkoff sound sensor but also the reference signal as noise, so that the sphygmomanometer is erroneously operated. A blood pressure measuring method utilizing as a reference signal a heartbeat synchronizing signal obtained by detecting cardioelectric potential has been developed for a considerably long period of time, but it is not practical due to a complicated step to detect cardioelectric potential.

The development of electronic circuits in recent years has brought an extra-small, inexpensive cardioelectric potential detector into existence, and made it possible to utilize heartbeats for sphygmomanometers conveniently. However, utilizing a heartbeat as a reference signal has some problems when the sphygmomanometer is used in a place in which noise or vibration occurs. Since heartbeats are measured constantly, reference signals are generated irrespective of the level of arm band pressure. Consequently, a sphygmomanometer is operated erroneously due to noise even when the cuff is in a level far away from the range of cuff pressures in which real Korotkoff sounds occur. Taking a logical product of heartbeats and a regular reference signal based on pulse pressure variations seems to be a good method of preventing this inconvenience. However, when a reference signal causes a false pulse to occur due to vibration, and if the time of occurrence of the false pulse agrees with that of a heartbeat synchronizing pulse, a plurality of pulses are generated per heartbeat synchronizing pulse if a method of taking such a logical product is employed. Therefore, heartbeats cannot be used as reliable reference signals.

In a conventional method of determining the presence of Korotkoff sounds, both the Korotkoff sound pulses and the Korotkoff sound reference signal are read into a CPU where they are compared by software. This method is advantageous in that its hardware is simple because the two signals are read directly into the CPU, but has a problem concerning loading on the software in that the relationship between the Korotkoff sound reference signal and the Korotkoff sound pulses must be examined continuously, or that a multiplexing interruption method must be used. The loading on the software not only causes problems in the arithmetical processing speed, but also the number of programs themselves is increased when the CPU is used for executing other operations as well as the blood pressure measurement.

SUMMARY OF THE INVENTION

An object of this invention is to provide an electronic sphygmomanometer capable of being operated stably with respect to noise and vibration.

Another object of this invention is to provide an electronic sphygmomanometer which is adapted to make optimum heartbeat-synchronizing pulses as reference signals for the determination of Korotkoff sounds.

Another object of this invention is to provide a circuit for determining the presence of Korotkoff sounds, and which does not have an increased number of hardware components and which has an extremely simplified software.

Another object of this invention is to provide an electronic sphygmomanometer using a full-wave rectifying means which is simple and convenient in construction and which is inexpensive.

Another object of this invention is to provide an electronic sphygmomanometer having a highly noise resistant signal comparator.

The above and other objects of this invention are carried out by an electronic sphygmomanometer including a Korotkoff sound detecting circuit, a cuff pressure detecting circuit having a pressure sensor and an Analog-to-Digital converter (called A/D converter hereinafter), reference signal generating means, a central processing unit (called CPU hereinafter) for receiving an output of the Korotkoff sound detecting circuit, an output of the reference signal generating means and an output of the pressure detecting circuit and determining a systolic and diastolic blood pressures, and a display unit for receiving an output of the CPU and displaying the systolic and diastolic blood pressures. The electronic sphygmomanometer comprises a cardioelectric potential detecting circuit having an one-shot pulse generating circuit for detecting a cardioelectric potential and producing a cardioelectric potential synchronizing signal, and the reference signal generating means includes a memory circuit for receiving the signal based on a pulsatile blood pressure variation within brachial artery and the cardioelectric potential synchronizing signal.

BRIEF DESCRIPTION OF THE DRAWINGS

FIG. 2 is the relation between a method of determining systolic and diastolic blood pressures and cardioelectric potential;

FIG. 11 is a graph of the relationship between cuff pressure and Korotkoff sounds when blood pressure is being measured;

FIG. 12 is a circuit diagram of a full-wave rectifier used in an electronic sphygmomanometer;

DETAILED DESCRIPTION OF THE PREFERRED EMBODIMENTS

Figure 1:
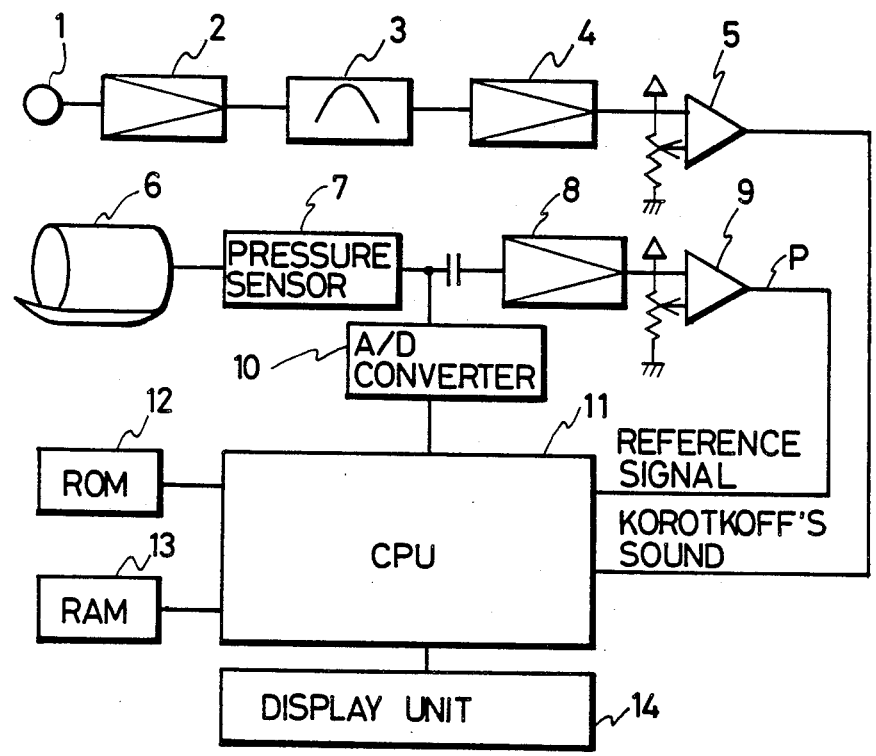
FIG. 1 is an example of a conventional electronic sphygmomanometer.

FIG. 1 shows an example of a conventional electronic sphygmomanometer, and FIG. 2 shows the relation between a method of determining systolic and diastolic blood pressures and cardioelectric potential. First, the principle of measuring blood pressure will be described. When the pressure of a cuff 6 wound around the upper arm is decreased gradually, Korotkoff sounds occur. The Korotkoff sounds are picked up by a Korotkoff sound sensor 1 to be extracted as digital pulses by a comparator 5 through an amplifier 2, a filter 3 and an amplifier 4. The pressure in the cuff 6 is converted into an electric signal through a pressure sensor 7 to be read into a CPU 11 through an A/D converter 10. On the other hand, as shown in FIG. 2, pressure variations based on a pulsatile blood pressure variation within a brachial artery occur from a period of time before the time during which Korotkoff sounds occur to a period of time thereafter. These variations are determined clearly by amplifying variations in an output from the pressure sensor 7 by an amplifier 8 and converted into a digital pulse in a comparator 9. This pulse is a pulse pressure variation pulse P shown in FIGS. 4 and 5. This pulse pressure variation pulse P is introduced into the CPU 11 as a reference signal for use in detecting Korotkoff sounds. The CPU 11 is adapted to process each signal in accordance with a program in a ROM 12 to determine a systolic and a diastolic blood pressure, which are indicated on a display unit 14. Reference numeral 13 denotes a RAM. However, it can be imagined easily that, when a cuff, a rubber tube or a rubber ball is vibrated, pressure variations occur, which are detected to generate an erroneous reference signal.

Figure 3A:
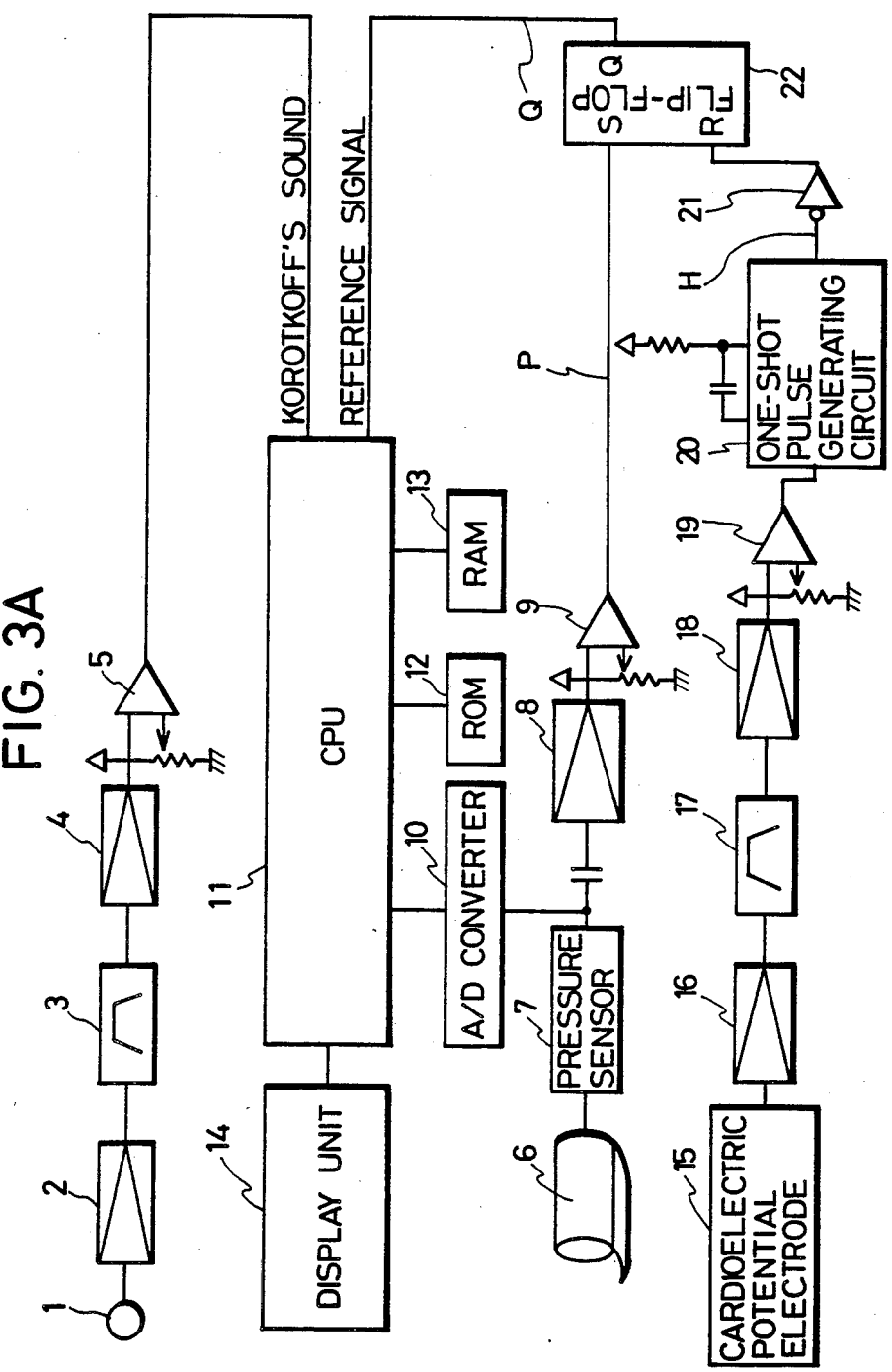
FIG. 3A is an embodiment of an electronic sphygmomanometer according to this invention.

FIG. 3A is a block diagram of an embodiment of this invention. The embodiment is provided additionally with parts 15, which designates a cardioelectric potential electrode, to 22, which designates a flip-flop, as compared with the sphygmomanometer shown in FIG. 1. The cardioelectric potential picked up by the electrode 15 is re-amplified by an amplifier 18 through an amplifier 16 and a filter 17 to be converted into a digital pulse by a comparator 19. This pulse causes a one-shot pulse generating circuit 20 to be triggered to produce a heartbeat synchronizing pulse H of a constant width. A heartbeat synchronizing pulse outputting terminal of the circuit 20 is connected to a resetting terminal of the flip-flop 22 through an inverter 21. Accordingly, when no heartbeat synchronizing pulse is generated, an output terminal of the flip-flop 22 remains to be reset even if the pressure in the cuff 6 varies. While a heartbeat synchronizing pulse H is generated, the flip-flop 22 is released from the resetting power. When pulse pressure variations occur with the flip-flop 22 in this state, the flip-flop is set and continues to be in the same set state until the heartbeat synchronizing pulse H terminates. An output Q from the flip-flop 22 is used as a reference signal.

Figure 3B:
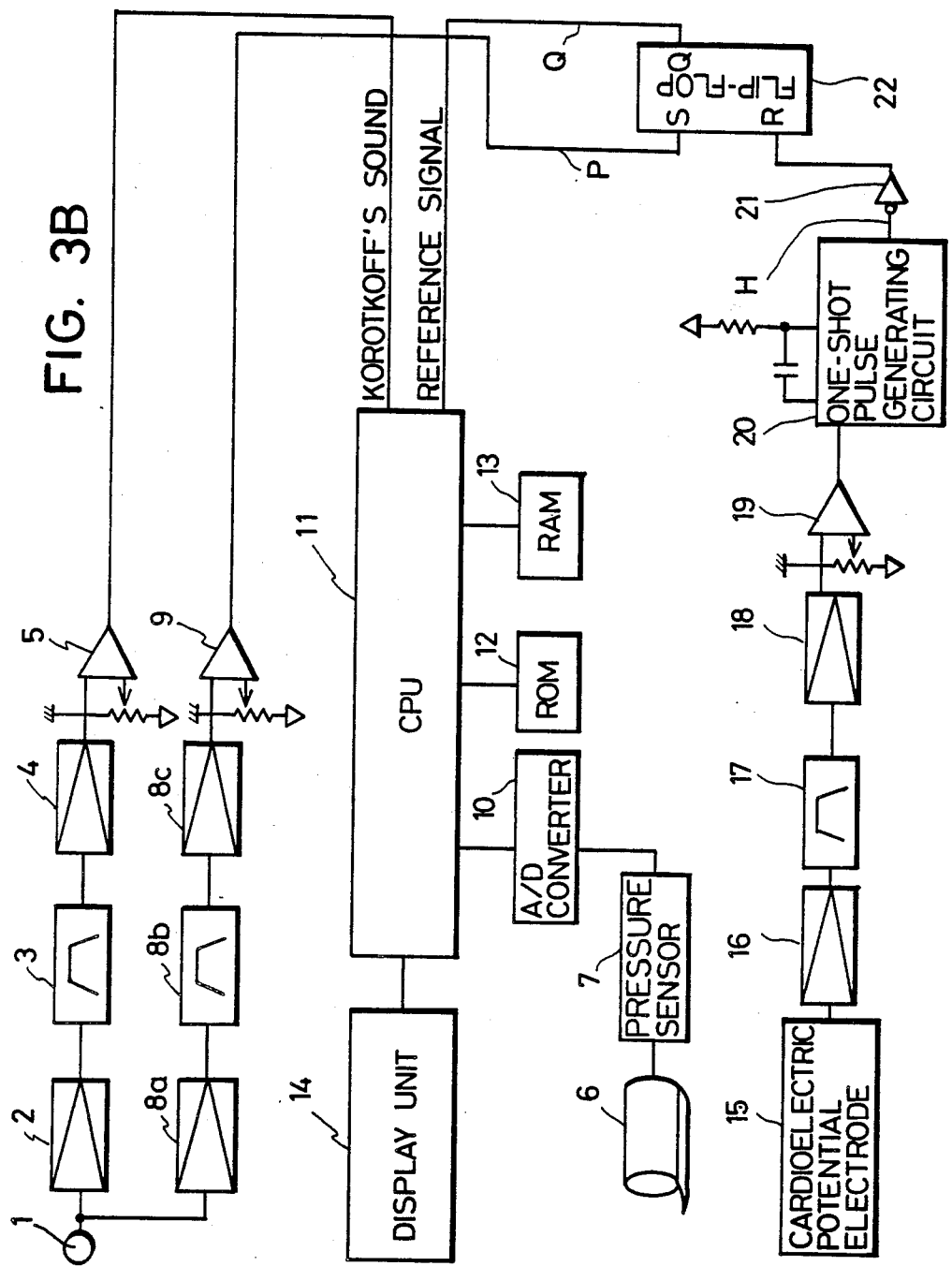
FIG. 3B is another embodiment of an electronic sphygmomanometer according to this invention.

FIG. 3B shows another embodiment of this invention. In this embodiment, a pulse pressure variation pulse generating means including Korotkoff sound sensor 1, amplifiers 8a and 8c, a filter 8b, and the comparator 9 is different from that of the embodiment as shown in FIG. 3A.

Figure 4:
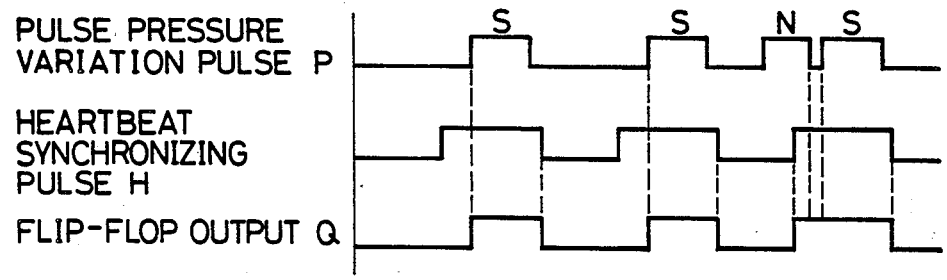
FIG. 4 is a timing chart for the embodiments of FIGS. 3A and 3B.
Figure 5A:
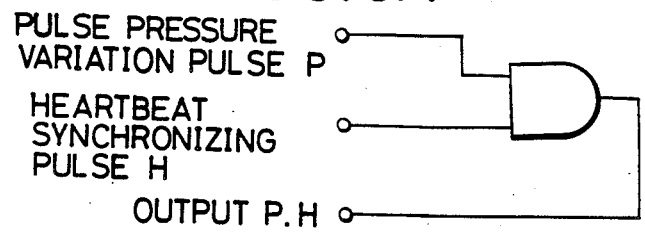
FIGS. 5A and 5B are diagrams for describing the embodiments of FIGS. 3A and 3B.
Figure 5B:
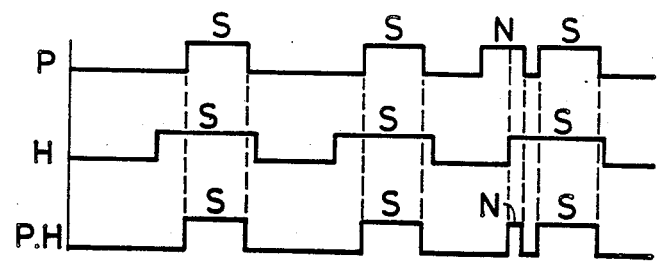

FIG. 4 is a chart showing the timing of the generation of various pulses in the above-described operation. If a logical product P·H of a heartbeat synchronizing pulse H and a pulse pressure variation pulse P as shown in FIG. 5A is taken simply as a reference signal, excess pulses are generated as reference signals when a false pulse N is generated as a pulse pressure variation pulse P due to the vibration of the cuff 6 at the same instant as a heartbeat synchronizing pulse H and continues for the same period of time as the same pulse H, as shown in FIG. 5B. This causes the sphygmomanometer to be operated erroneously during the measurement of blood pressure for the following reasons. In case the condition exists in which a reference signal is detected with no detected Korotkoff sounds and such condition continues for a certain period of time, the pressure at a time when a final Korotkoff sound occurs is determined as a diastolic blood pressure.

Figure 6:
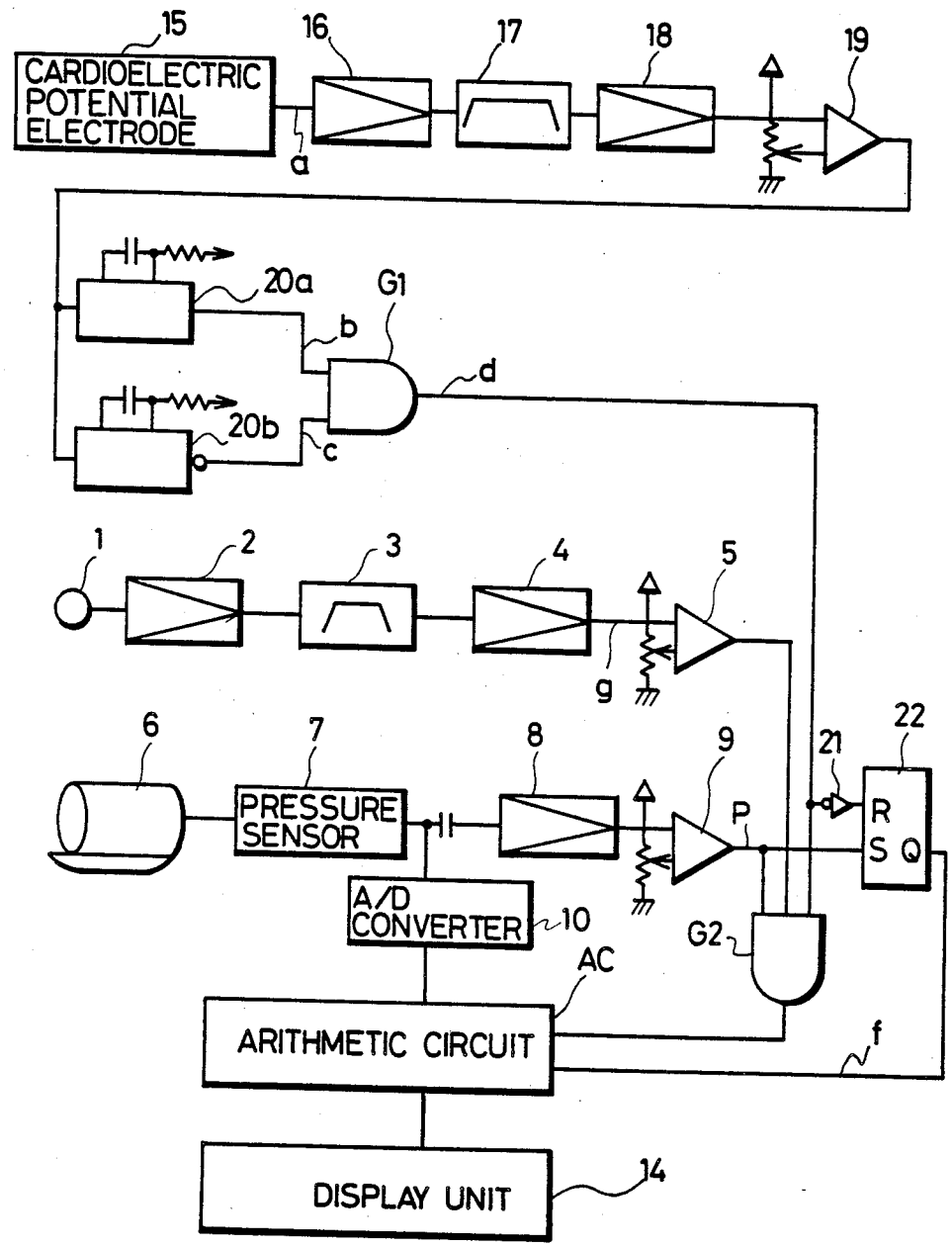
FIG. 6 is a block diagram of another embodiment according to this invention.
Figure 7:
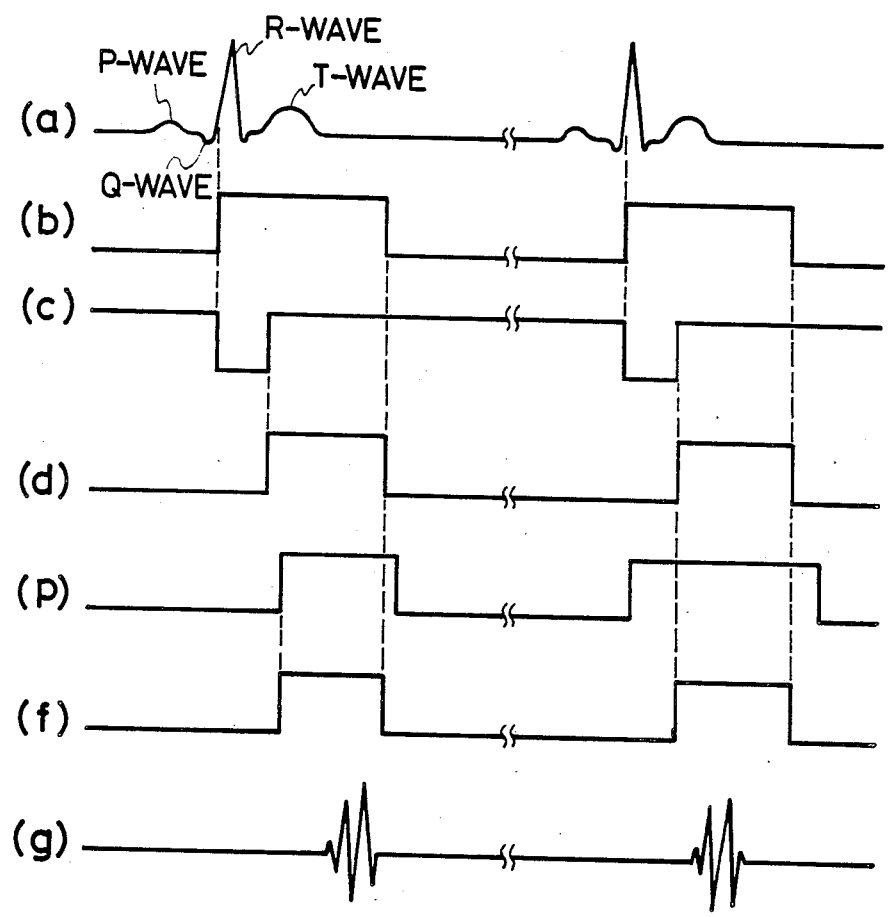
FIG. 7 is a chart showing the timing of operations of various parts of the embodiment as shown in FIG. 6.

Referring to FIG. 6 showing another embodiment of this invention, the cardioelectric potential obtained through a cardioelectric potential electrode 15 passes through an amplifier 16 and a filter 17 to be further amplified by an amplifier 18 and then extracted as a digital pulse from a comparator 19. This pulse causes one-shot circuits 20a, 20b to be triggered to generate pulses having predetermined time widths, a logical product of which is taken by an AND-gate G1. FIG. 7 is a timing chart. Reference letter (a) denotes the cardioelectric potential signal, and (b), (c) denote output signals from the one-shot circuits 20a, 20b. The output (b) from the one-shot circuit 20a is longer than the output (c) from the one-shot circuit, and the phases of the one-shot circuits 6a, 6b are opposite to each other. Reference letter (d) denotes an output signal from the AND-gate G1. The signal widths of the one-shot circuits 20a, 20b are preferably 250–350 mS and 50–150 mS, respectively. Referring to FIG. 6 again, a sound obtained from a Korotkoff sound sensor 1 passes through an amplifier 2 and is extracted by a filter 3. This Korotkoff sound is amplified by an amplifier 4 to be then detected as a digital pulse by a comparator 5. The air pressure in cuff 6 is extracted as a voltage through a pressure sensor 7, and this voltage is read into an arithmetic circuit AC through an A/D converter 10. On the other hand, only such variations in pressure based on a pulsatile blood pressure variation within a brachial artery are amplified by an amplifier 8 to be formed into a digital pulse by a comparator 9. Outputs from the AND-gate G1 and comparator 9 are applied to a flip-flop 22 to be utilized as a reference signal. An AND-gate G2 is provided so as to reduce the probability of occurrence of an erroneous operation due to noise by limiting the time for the detection of Korotkoff sounds. Taking a logical product of the reference signal and Korotkoff sounds is also done in the arithmetic circuit AC by utilizing software. Each signal is processed in the arithmetic circuit AC, and systolic and diastolic blood pressures are indicated on a display unit 14.

Reference letter (P) in FIG. 7 denotes an output signal generated in the comparator 9 due to variations in pressure based on a pulsatile blood pressure variation within a brachial artery. Unlike heartbears, Korotkoff sounds are measured in a comparatively narrow range including the range of cuff pressure in which Korotkoff sounds occur, and the pulse width and position relative to R-wave component of the cardioelectric signal are not constant. Reference letter (g) denotes a Korotkoff sound signal. The flip-flop 22 receives both the output signal (d) from the AND-gate G1 and pulse pressure variation signal (P) and produces an output signal (f). A signal generated in this period of time alone is used as a reference signal, so that a false reference signal due to variations in pressure ascribed to the pulsation of the cuff or a rubber tube, which false signal causes an erroneous operation of the sphygmomanometer, is not generated. Since the time for a heartbeat synchronizing pulse is definitely limited, the frequency in picking up noise is reduced. Unlike a sphygmomanometer using only a heartbeat synchronizing signal as a reference signal, the sphygmomanometer as shown in FIG. 6 is capable of predicting a pressure under which Korotkoff sounds occur.

Figure 8:
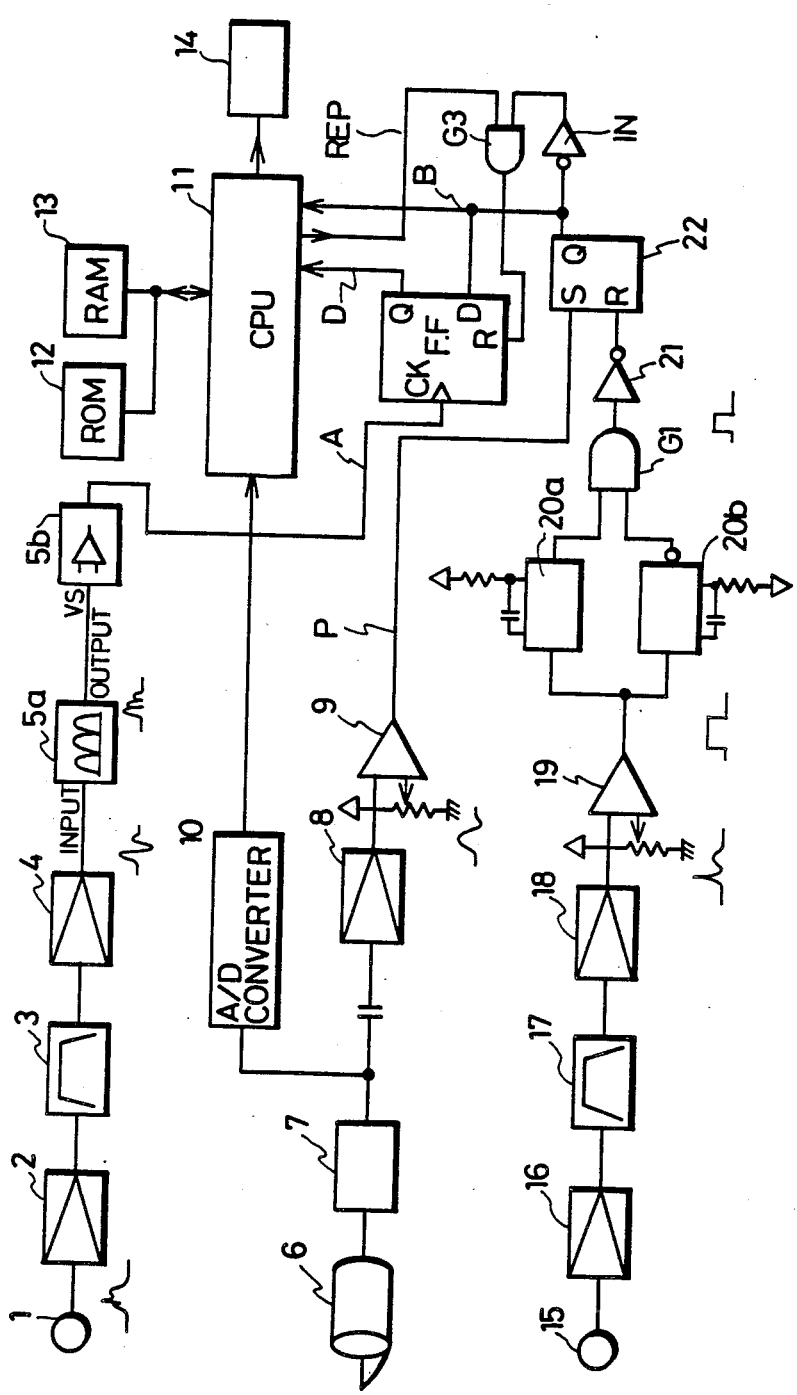
FIG. 8 is another embodiment according to this invention.

FIG. 8 shows another embodiment of this invention. The advantages of a flip-flop 22 and one-shot circuits 20a and 20b were already described above. Accordingly, the features and advantages of other parts of this embodiment will be described with reference to FIGS. 9–20.

Figure 9:
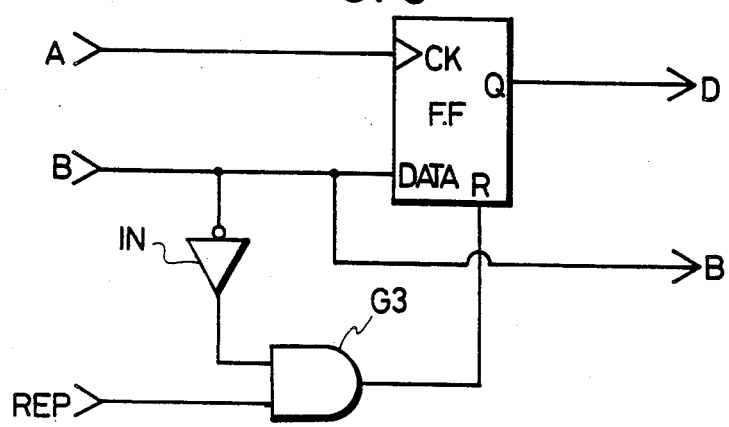
FIG. 9 is a circuit diagram used in an electronic sphygmomanometer according to this invention of FIG. 8.

FIG. 9 is a circuit employed in the part of the embodiment in FIG. 8. This circuit exists between the flip-flop 22 and the CPU as understood from FIG. 8.

Figure 10:
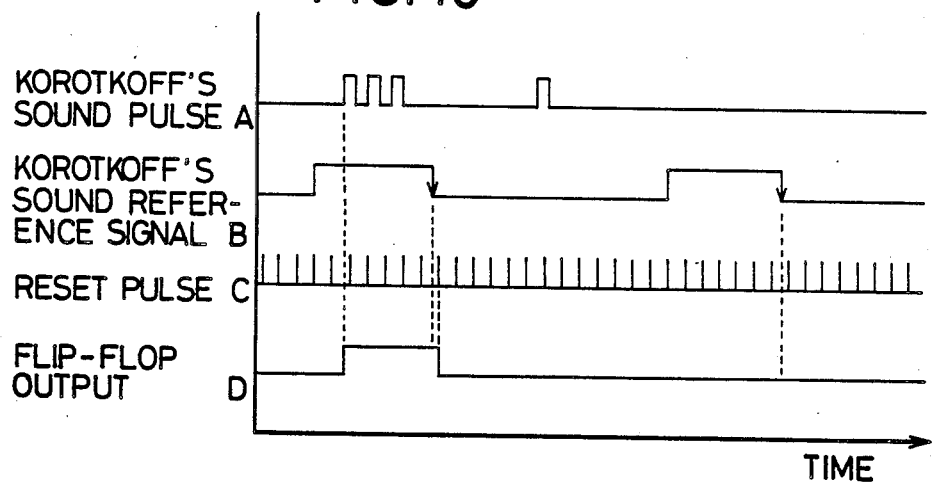
FIG. 10 is a timing chart of the various signal as shown in FIG. 9.

FIG. 10 is a graph of the relationships between the various signals. When a Korotkoff sound reference signal B is not generated, the data of a flip-flop F.F is at a low level, and the output of an inverter IN is at a high level. As a result, the reset terminal of the flip-flop F.F is always supplied with reset pulses REP through an AND-gate G3, so that even if Korotkoff sound pulses A are generated, not by real Korotkoff sounds but by noise, the output D of the flip-flop F.F is fixed at the low level. Consider the case in which, while the Korotkoff sound reference signal B is at the high level, Korotkoff sounds are generated so that Korotkoff sound pulses A are input. At this stage, the flip-flop F.F reads in the Korotkoff sound reference signal B at the rise of each of the Korotkoff sound pulses A so that its output D goes high. This state is maintained while the Korotkoff sound reference signal B is at the high level. When the Korotkoff sound reference signal B returns to the low level, the AND-gate G3 is opened by the inverter IN so that the flip-flop F.F is reset by the next reset pulse REP to return the output D to the low level with a delay after the Korotkoff sound reference signal B. While no Korotkoff sounds are being generated, the flip-flop output D remains at the low level. In this way, the judgement of the presence of Korotkoff sounds is conducted by examining the output D of the flip-flop F.F when the Korotkoff sound reference signal B falls.

When a sphygmomanometer is designed using this circuit, the CPU is interrupted at the end of the Korotkoff sound reference signal B so that the output D of the flip-flop F.F at that time can be examined. For example, a method could be used by which the output D of the flip-flop F.F is input as the data of a parallel I/O controller (called PIO hereinafter), and the interruption is conducted at the end of the Korotkoff sound reference signal B by using this signal B itself as a strobe signal for the PIO. It is a general requirement that the data is stable during a certain time period before and after the interruption. It is, therefore, important that the flip-flop F.F is reset with some delay after the Korotkoff sound reference signal. B. Since the presence of Korotkoff sounds can be determined in this manner by a single interruption, the loading on the software in the CPU can be greatly reduced. With this reduction of the arithmetical period, the program is accordingly shortened. This circuit of FIG. 9 can provide its effects especially when the sphygmomanometer must be designed with a limited memory size. From the point of view of hardware, on the other hand, only a small number of components must be added. However, this addition will not reduce the effects, since the effect of the cost reduction should be very high if the cost of developing the software, the cost of the multiple interruption function of the CPU itself, and the memory size are taken into consideration.

The graphs (a) and (b) of FIG. 11 illustrate the relationship between cuff pressure and Korotkoff sounds when blood pressure is being measured. As the cuff pressure is reduced, Korotkoff sounds are generated until they disappear. The cuff pressure at the generation and disappearance of Korotkoff sounds provide the systolic and diastolic blood pressures, but the direction in which the maximum amplitudes of Korotkoff sounds occurs is not fixed. As can be understood, therefore, for efficient detection, a full-wave rectifier 5a must be provided upstream of the comparator 5b as shown in FIG. 8.

FIG. 12 is a circuit diagram of a rectifier 5a employed in the embodiment of FIG. 8. For a positive input, the output of an operational amplifier Q1 is cut off by a rectifying element D2 so that the input is transmitted unchanged as an output through a rectifying element D1. For a negative input, on the other hand, the rectifying element D1 is open so that the operational amplifier Q1 acts as an inverting amplifier with an amplification factor of R2/R1, i.e., the ratio of the resistances of resistors R1 and R2. During this time, the rectifying element D2 is conductive. The resistances of the resistors R1 and R2 are usually made equal. The circuit thus constructed has linearity and zero-crossing problems because of the forward voltage drop and the operating resistance of the rectifying elements D1 and D2. These problems are not, however, serious enough to affect the requirements of a rectifier in the first stage of a comparator.

The fact that only a single operational amplifier performs the full-wave rectification in the full-wave rectifier has the result of reducing the number of components and the cost. This effect of the full-wave rectifier is best exploited when a package containing a plurality of operational amplifiers is used, and when two operational amplifiers are used in a full-wave rectifier, only one of them can not be used as an operational amplifier of another package.

Figure 13:
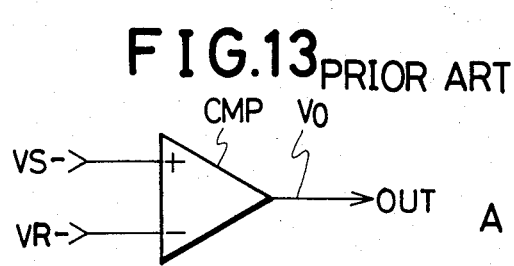
FIG. 13 is a circuit diagram of the fixed reference potential type of signal comparator of the prior art.
Figure 14:
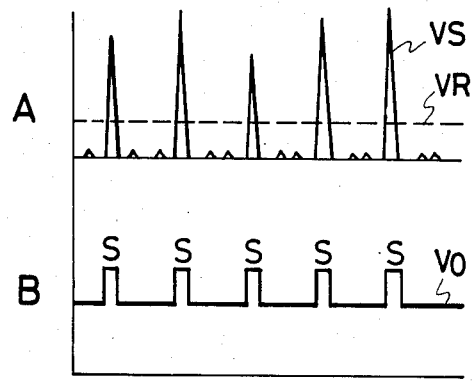
FIG. 14 is a graph of the input and output signals for low-level noise to describe the circuit diagram of FIG. 13.
Figure 15:
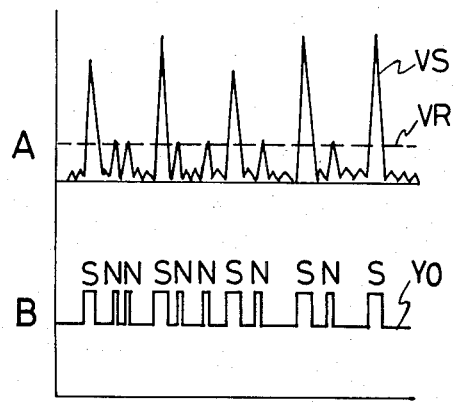
FIG. 15 is a graph of the input and output signals to describe the circuit diagram of FIG. 14 when noise is present.

FIG. 13 shows a fixed reference potential type of signal comparator which is widely used conventionally. The output VO of a comparator CMP changes only when an input signal VS exceeds a reference potential VR. The relationship between input and output of that stage is illustrated at A and B in FIG. 14, and at A and B in FIG. 15. Since the reference potential VR is fixed, the comparator is effective for an input signal VS that has a relatively low level of noise, as illustrated in FIG. 14, but the number of erroneous detections increases with increasing noise, as illustrated in FIG. 15. If, in this case, the reference potential VR is raised, the number of erroneous detections by the comparator due to noise decreases, but its sensitivity to the input signal VS drops in a low-noise environment. The term "noise" as used herein includes that noise which is generated within the human body but is outside the scope of the measurements, in addition to vibrations, noise and other noise generated by the influence of the electromagnetism of the meter including the sensor. The former type of noise is exemplified by the case in which muscular potentials are mixed with cardiac potentials as a result of vibrations within the human body.

Figure 16:
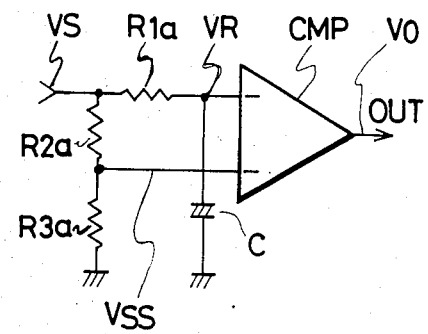
FIG. 16 is a circuit diagram of the varying reference potential type of signal comparator of the prior art.
Figure 17:
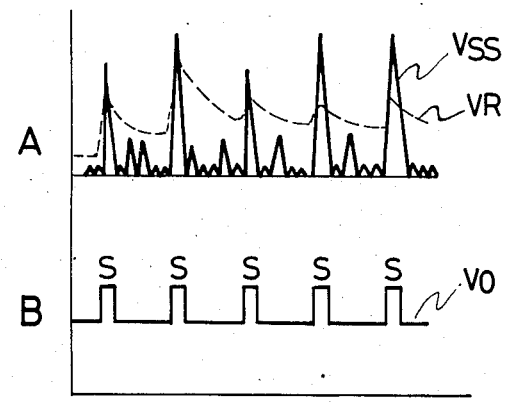
FIG. 17 is a graph of the input and output signals for low-level noise to describe the circuit diagram of FIG. 16.
Figure 18:
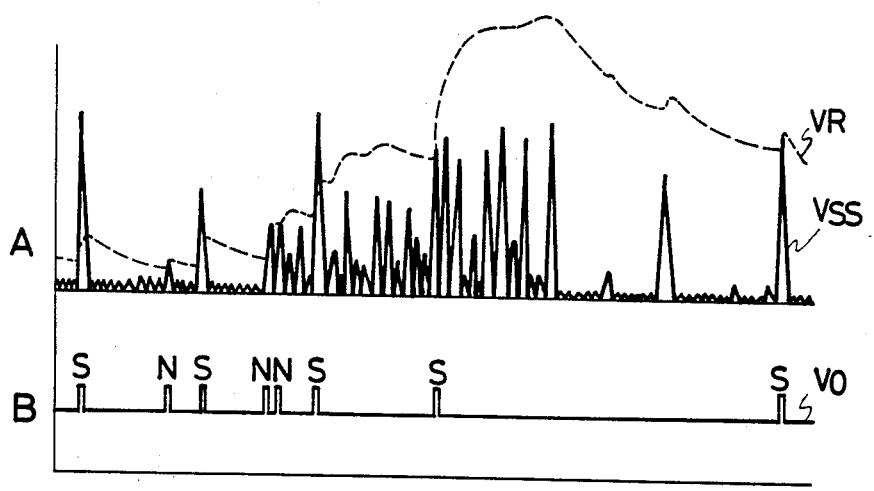
FIG. 18 is a graph of the input and output signals to describe the circuit diagram of FIG. 16 when noise varies markedly.

One prior art circuit for reducing the effects of these types of noise uses a varying reference potential type of signal comparator which is shown in FIG. 16. In this comparator, the input signal is integrated by a resistor R1a and a capacitor C, and the integrated signal with a certain time constant is applied to a reference input potential terminal VR. Since, however, the input voltage VS is relatively too large as it is, the signal is divided by resistors R2a and R3a and is used as an input to a comparator signal input terminal VSS. FIG. 17 illustrates the relationships between the comparator input signal VSS, the reference potential VR and the output VO, when the input signal VS contains a low level of noise. FIG. 18 illustrates the relationships when a signal with a widely varying level of noise is input. Under low-noise conditions, the reference potential VR becomes so excessively low that even low levels of noise are detected. In an environment in which there is a lot of noise at the same level as that of the input signal VS, on the other hand, the resistance-divided signal is applied to the comparator signal input terminal VSS, but the reference potential can theoretically rise to a maximum of the level of the input signal itself. As a result, it could happen that no signal detection is conducted immediately after a shift from a high-noise environment to a low-noise environment, as illustrated in FIG. 18.

Figure 19:
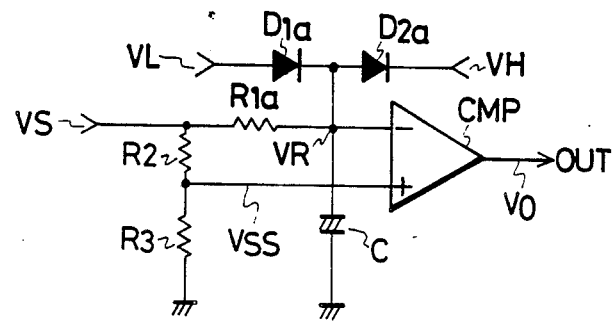
FIG. 19 is a circuit diagram of a signal comparator used in an electronic sphygmomanometer according to this invention.
Figure 20:
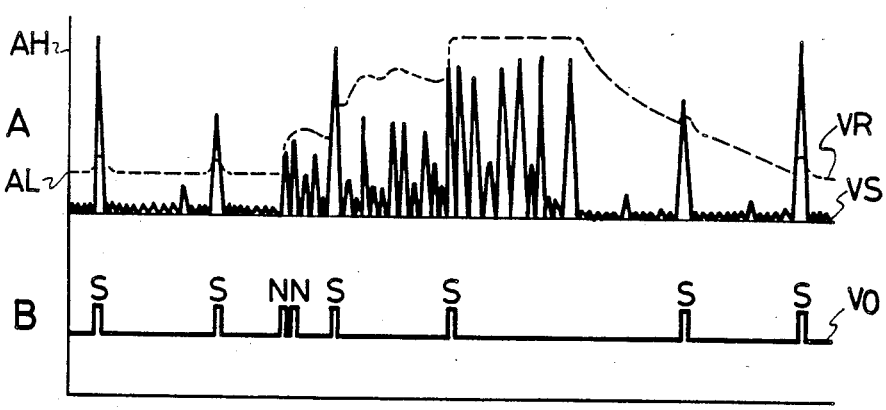
FIG. 20 is a graph of the relationship between the signal input of FIG. 18 and the output signal of the signal comparator as shown in FIG. 19.

FIG. 19 shows an embodiment of the comparator 5b employed in the embodiment of FIG. 8. The difference from the construction of FIG. 16 lies in that the reference potential is connected through a diode D1a to a lower-limit setting potential VL, and through a diode D2a to an upper-limiting setting potential VH. FIG. 20 illustrates the relationships between the comparator input signal VSS, the reference potential VR, and the output VO, with the same input signal VS as that of FIG. 18. In the low-noise environment, the reference potential VR does not drop so low that low level noises are detected. It can also be seen that when the level of noise abruptly drops from a high level, the reference potential VR also drops to prevent detection mistakes. It is desirable that a maximum value of the signal being detected and a maximum value of noise are restricted in advance. If this restricted value is designated by $V_{max}$, the upper-limit setting potential VH is determined by the following inequality:

$$VH > V_{max} \cdot R3/(R2+R3),$$

where R2a and R3a are the resistances of the resistors R2a and R3a, respectively.

The lower-limit setting potential VL has to be determined by considering the relationship between the signal component being measured and the noise component.

According to the signal comparator employed in the embodiment of this invention, it is capable of accurately following noise changes even in the environment with extreme noise variations, and the signal comparator can be constructed by merely adding a small number of parts to the varying reference potential type of signal comparator of the prior art. When the comparator is mounted on a vehicle, for example, the noise environment can be dramatically changed by abrupt starts or stops or by changes in the road surface conditions. The signal comparator can also be applied to a detector of Korotkoff sounds in a sphygmomanometer mounted on a vehicle, so that a stable signal can be detected even within the vehicle. Therefore, this signal comparator is not only highly effective in the field of emergency medical treatment, but can contribute to a widening of the range of medical services available, thanks to the advantage it provides that measurements can be conducted anywhere.

What is claimed is:

1. In an electronic sphygmomanometer including a Korotkoff sound detecting circuit, a cuff pressure detecting circuit having a pressure sensor, an analog-to-digital converter connected to the cuff pressure detecting circuit, reference signal generating means for producing a reference signal relating to a signal based on a pulsatile blood pressure variation within a brachial artery, central processing unit means for receiving a signal relating to an output of the Korotkoff sound detecting circuit, an output of the reference signal generating means and an output of the cuff pressure detecting circuit through the analog-to-digital converter and determining a systolic and a diastolic blood pressure, and display unit means for receiving an output of the central processing unit means and displaying the systolic and diastolic blood pressures, the improvement comprising: cardioelectric potential detecting circuit means having a one-shot pulse generating circuit for detecting a cardioelectric potential and producing a cardioelectric potential synchronizing signal; and the reference signal generating means including memory circuit means for receiving the signal based on a pulsatile blood pressure variation within a brachial artery and the cardioelectric potential synchronizing signal.

2. An electronic sphygmomanometer as claimed in claim 1, wherein the one-shot pulse generating circuit has means for producing a one-shot signal 50-150 ms after a detection of an R-wave.

3. An electronic sphygmomanometer as claimed in claim 1, further comprising Korotkoff sound memory circuit means between the reference signal generating means and the central processing unit means, said Korotkoff sound memory circuit means memorizing the output of the Korotkoff sound detecting circuit until the reference signal terminates after the Korotkoff sound memory circuit means detects the output of the Korotkoff sound detecting circuit while the reference signal exists.

4. An electronic sphygmomanometer as claimed in claim 1, wherein the Korotkoff sound detecting circuit includes a Korotkoff sound detector for detecting Korotkoff sound and producing a Korotkoff sound signal, rectifier means for rectifying the Korotkoff sound signal, and comparator means for detecting a signal level connected to the rectifier means.

5. An electronic sphygmomanometer as claimed in claim 4, wherein the comparator means includes at least one rectifying element through which a reference input terminal of the comparator means is connected to a first predetermined potential to set a lower and/or upper limit for a reference input voltage, the reference input terminal being connected through a first resistive element to an output of the rectifier means and through a capacitive element to a second predetermined potential, and a signal input terminal of the comparator means being connected to a second resistive element which receives the output of the rectifier means, and a third resistive element connected to the second resistive element.

6. In an electronic sphygmomanometer having Korotkoff sound detecting means for detecting a person's Korotkoff sounds and producing a corresponding Korotkoff sound signal, and cuff pressure detecting means for detecting the person's pulsatile blood pressure variation within a brachial artery and producing a corresponding blood pressure signal: cardioelectric potential detecting means for detecting the person's cardioelectric potential and producing a cardioelectric potential synchronizing pulse signal indicative of the person's heartbeat; reference signal generating means responsive to the blood pressure signal and synchronizing pulse signal for producing a reference signal only during the existence of the synchronizing pulse signal; and circuit means responsive to the blood pressure signal, Korotkoff sound signal and reference signal for determining the person's systolic and diastolic blood pressures.

7. An electronic sphygmomanometer according to claim 6; wherein the cardioelectric potential detecting means includes means for producing a cardioelectric potential synchronizing pulse signal of constant pulse width for each detected heartbeat.

8. An electronic sphygmomanometer according to claim 7; wherein the means for producing a cardioelectric potential synchronizing pulse signal comprises a one-shot pulse generating circuit.

9. An electronic sphygmomanometer according to claim 7; wherein the reference signal generating means includes memory means connected to receive the blood pressure signal and synchronizing pulse signal for memorizing the blood pressure signal during the pulse period of the synchronizing pulse signal.

10. An electronic sphygmomanometer according to claim 9; wherein the memory means comprises a flip-flop circuit.

11. An electronic sphygmomanometer according to claim 6; wherein the means for producing a cardioelectric potential synchronizing pulse signal comprises a one-shot pulse generating circuit.

12. An electronic sphygmomanometer according to claim 11; wherein the one-shot pulse generating circuit has means for producing a one-shot pulse signal 50-150 ms after detection of an R-wave of the person's cardioelectric potential.

13. An electronic sphygmomanometer according to claim 6; wherein the reference signal generating means includes memory means connected to receive the blood pressure signal and synchronizing pulse signal for memorizing the blood pressure signal during the pulse period of the synchronizing pulse signal.

14. An electronic sphygmomanometer according to claim 13; wherein the memory means comprises a flip-flop circuit.

* * * * *